US012399075B2

(12) United States Patent
Dong

(10) Patent No.: US 12,399,075 B2
(45) Date of Patent: Aug. 26, 2025

(54) PIPELINE PRESSURE MONITORING DEVICE

(71) Applicant: SCINOMED(SHANGHAI)BIO-TECH Co., Ltd., Shanghai (CN)

(72) Inventor: Yadong Dong, Shanghai (CN)

(73) Assignee: SCINOMED(SHANGHAI)BIO-TECH CO., LTD., Shanghai (CN)

( * ) Notice: Subject to any disclaimer, the term of this patent is extended or adjusted under 35 U.S.C. 154(b) by 299 days.

(21) Appl. No.: 18/037,485

(22) PCT Filed: Dec. 31, 2020

(86) PCT No.: PCT/CN2020/141900
§ 371 (c)(1),
(2) Date: May 17, 2023

(87) PCT Pub. No.: WO2022/105036
PCT Pub. Date: May 27, 2022

(65) Prior Publication Data
US 2024/0011860 A1 Jan. 11, 2024

(30) Foreign Application Priority Data
Nov. 17, 2020 (CN) .......................... 202011287588.5

(51) Int. Cl.
A61M 5/168 (2006.01)
G01L 19/00 (2006.01)
G01L 19/14 (2006.01)

(52) U.S. Cl.
CPC ..... *G01L 19/0038* (2013.01); *A61M 5/16854* (2013.01); *G01L 19/142* (2013.01)

(58) Field of Classification Search
CPC ... G01L 19/0038; G01L 19/142; G01L 11/00; G01L 19/143; G01L 19/003; A61M 5/16854; G01B 7/003
See application file for complete search history.

(56) References Cited

U.S. PATENT DOCUMENTS

| 5,235,324 A | * | 8/1993 | Gagnebin | .............. | H01H 35/24 200/82 R |
| 2010/0274180 A1 | * | 10/2010 | Donovan | .......... | A61M 5/16854 703/2 |

(Continued)

FOREIGN PATENT DOCUMENTS

| CN | 101349604 A | 1/2009 |
| CN | 101786450 A | 7/2010 |

(Continued)

*Primary Examiner* — David J Bolduc
(74) *Attorney, Agent, or Firm* — MUNCY, GEISSLER, OLDS & LOWE, P.C.

(57) ABSTRACT

A pipeline pressure monitoring device includes a housing, a vent nozzle, a first circuit board, a pressure sensor, a sliding sleeve, an elastic member sleeved on the vent nozzle and sandwiched between the first stop block and the sliding sleeve, a magnetic block on the sliding sleeve, a second circuit board connected to the first circuit board, and a position sensor on the second circuit board and cooperating with the magnetic block. A first stop block is arranged on the vent nozzle. One end of the vent nozzle protrudes from the housing through a mounting hole of the housing. The pressure sensor is installed at the other end of the vent nozzle and on the first circuit board. The pressure sensor blocks the other end of the vent nozzle. The sliding sleeve is installed in the mounting hole in a sliding manner and sleeved on the vent nozzle.

5 Claims, 2 Drawing Sheets

(56) References Cited

U.S. PATENT DOCUMENTS

| | | | |
|---|---|---|---|
| 2015/0198501 A1* | 7/2015 | Rule | A61M 5/16854 |
| | | | 73/40.5 R |
| 2016/0361734 A1* | 12/2016 | Routen | B05C 5/02 |
| 2018/0196531 A1* | 7/2018 | Tsai | G06F 3/0383 |
| 2020/0016944 A1* | 1/2020 | Qiu | B60C 23/04 |

FOREIGN PATENT DOCUMENTS

| | | |
|---|---|---|
| CN | 205843873 U | 12/2016 |
| CN | 206670839 U | 11/2017 |
| CN | 107823741 A | 3/2018 |
| CN | 110595665 A | 12/2019 |
| CN | 110793709 A | 2/2020 |
| CN | 212830585 U | 3/2021 |

\* cited by examiner

PIPELINE PRESSURE MONITORING DEVICE

FIELD OF THE INVENTION

The present invention relates to a medical device, and more particularly to a pipeline pressure monitoring device.

BACKGROUND OF THE INVENTION

In medical device applications, especially blood processing equipment and blood component collection equipment, it is necessary to monitor the pressure of a system. While monitoring the pressure, it is necessary to monitor the installation of consumables. The mechanical structure of a conventional pressure monitoring device includes a guide cap, a guide cap fixing seat, a guide cap bracket, an elastic ring, an elastic ring fixing nut, a conical vent nozzle, a sealing ring, and a bracket. The guide cap is made of a plastic material. The elastic ring is made of rubber. The elastic ring is fitted on the outside of the conical vent nozzle and has a concave groove. The elastic ring is tightened and pressed on the conical vent nozzle by the elastic ring fixing nut. The guide cap is inserted into the concave groove of the elastic ring and fixed on the guide cap fixing seat. Due to its complex mechanical structure and materials, it has the following characteristics: complex structure, large volume, poor smoothness and short service life and it is damaged easily.

SUMMARY OF THE INVENTION

The present invention is to solve the above problems. The primary object of the present invention is to provide a pipeline pressure monitoring device, which has simple structure, small size, good smoothness and long service life and is not easily damaged The present invention provides a pipeline pressure monitoring device, comprising:
  a housing, one side of the housing having a mounting hole;
  a vent nozzle, the vent nozzle having a vent, the vent nozzle being installed in the housing, one end of the vent nozzle extending out of the housing via the mounting hole, a first stop block being provided on the vent nozzle;
  a first circuit board, installed in the housing;
  a pressure sensor, configured to detect pressure inside the vent nozzle, the pressure sensor being installed on the first circuit board and connected to the first circuit board, the pressure sensor being matched with another end of the vent nozzle facing an inside of the housing, the pressure sensor being installed at the another end of the vent nozzle facing the inside of the housing to block the another end;
  a sliding sleeve, installed in the mounting hole in a sliding manner, the sliding sleeve having a through hole, the sliding sleeve being sleeved on the vent nozzle via the through hole, a limit member being provided on the sliding sleeve, the limit member being located inside the housing;
  an elastic member, sleeved on the vent nozzle and sandwiched between the first stop block and the sliding sleeve;
  a magnetic block, installed on the sliding sleeve;
  a second circuit board, installed in the housing and connected to the first circuit board; and
  a position sensor, installed on the second circuit board and connected to the second circuit board, wherein the installation position of the position sensor meets that: after a consumable connector is installed on the vent nozzle, the distance that the sliding sleeve slides toward the inside of the housing is just enough to make the magnetic block move into a detection area of the position sensor.

Furthermore, in the pipeline pressure monitoring device provided by the present invention, a sealing ring is provided between the pressure sensor and the vent nozzle.

Furthermore, in the pipeline pressure monitoring device provided by the present invention, the elastic member is a spring.

Furthermore, in the pipeline pressure monitoring device provided by the present invention, a bushing is provided between the sliding sleeve and the vent nozzle, the bushing is fixed on the through hole of the sliding sleeve, and the bushing is slidably sleeved on the vent nozzle.

Furthermore, in the pipeline pressure monitoring device provided by the present invention, the cross-section of the end of the vent nozzle facing an outside of the housing gradually decreases toward the outside of the housing, the cross-section of the vent is constant, a section of the vent nozzle that is gradually tapered does not contact the through hole, and the bushing is located on one side of the through hole facing the inside of the housing.

The present invention provides the following advantages:

The present invention has simple structure, small size, good smoothness and long service life, and is not easily damaged

DETAILED DESCRIPTION OF THE PREFERRED EMBODIMENTS

For the technical means, creative features, objects and effects achieved by the present invention to be understood easily, the following embodiments will specifically illustrate the pipeline pressure monitoring device of the present invention, with reference to the accompanying drawings.

Figure 1:
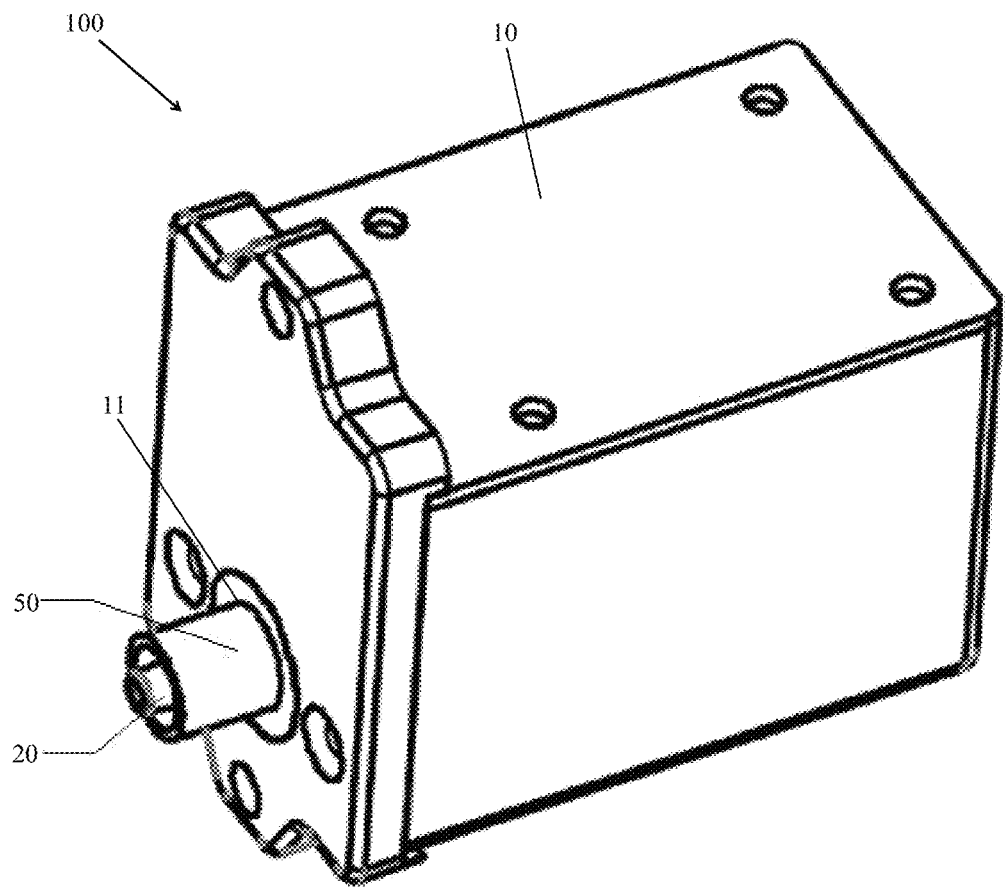
FIG. 1 is a perspective view of the pipeline pressure monitoring device according to an embodiment of the present invention.
Figure 2:
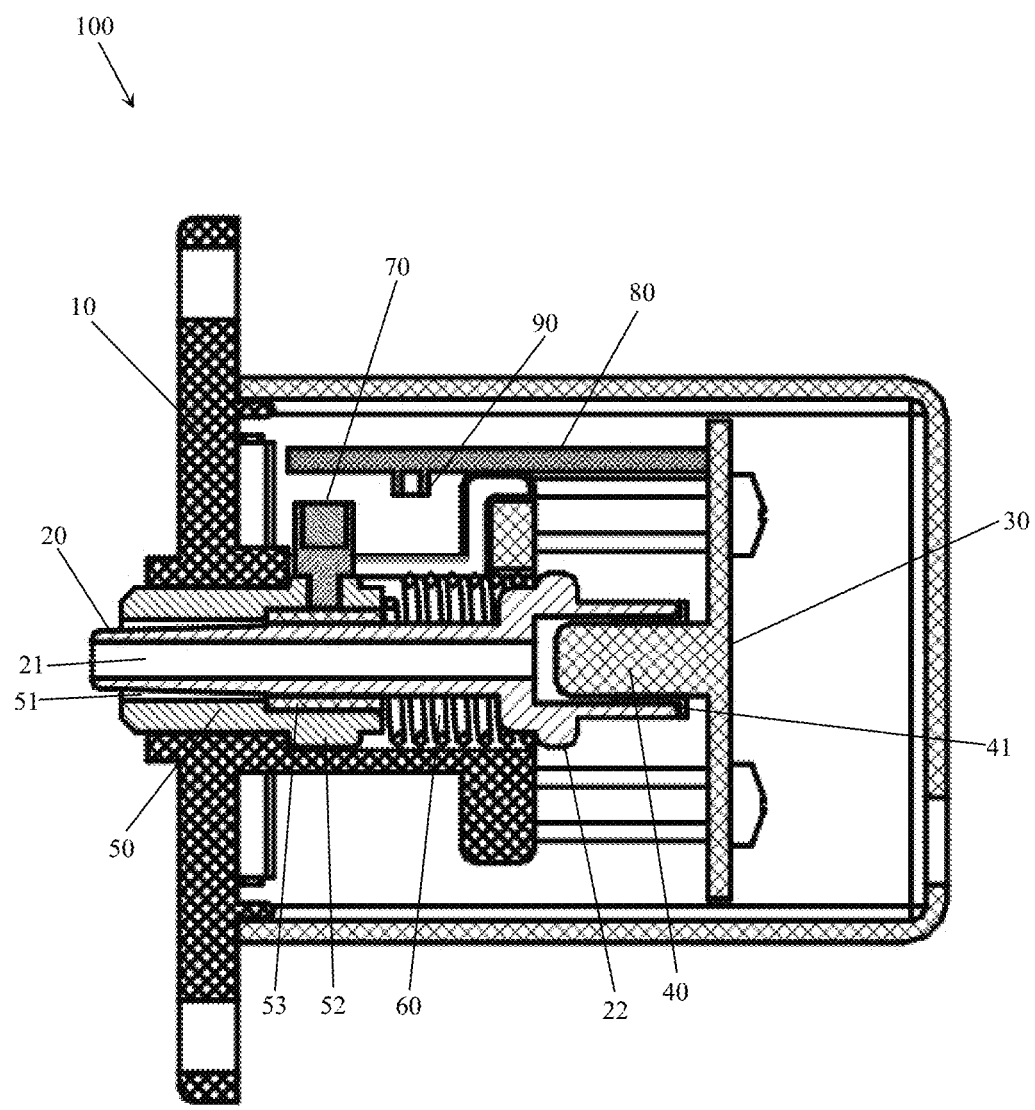
FIG. 2 is a cross-sectional view of the pipeline pressure monitoring device according to the embodiment of the present invention.

As shown in FIG. 1 and FIG. 2, the pipeline pressure monitoring device 100 comprises a housing 10, a vent nozzle 20, a first circuit board 30, a pressure sensor 40, a sliding sleeve 50, an elastic member 60, a magnetic block 70, a second circuit board 80, and a position sensor 90.

One side of the housing 10 has a mounting hole 11.

The vent nozzle 20 has a vent 21. The vent nozzle 20 is installed in the housing 10. One end of the vent nozzle 20 extends out of the housing 10 via the mounting hole 11. A first stop block 22 is provided on the vent nozzle 20.

The first circuit board 30 is installed in the housing 10. The pressure sensor 40 is configured to detect the pressure inside the vent nozzle 20. The pressure sensor 40 is installed on the first circuit board 30 and connected to the first circuit board 30. The pressure sensor 40 is matched with one end of the vent 21 facing the inside of the housing 10. The pressure sensor 40 is installed at the end of the vent 21 facing the inside of the housing 10 to block the end. After the vent nozzle 20 is installed on the pressure sensor 40, the first circuit board 30 and the pressure sensor 40 play a role in fixing the vent nozzle 20.

In this embodiment, a sealing ring 41 is provided between the pressure sensor 40 and the vent nozzle 20.

The sliding sleeve 50 is installed in the mounting hole 11 in a sliding manner. The sliding sleeve 50 has a through hole 51. The sliding sleeve 50 is sleeved on the vent nozzle 20 via the through hole 51. A limit member 52 is provided on the sliding sleeve 50. The limit member 52 is located inside the housing 10, and is configured to prevent the sliding sleeve 50 from sliding out of the mounting hole 11.

In the present embodiment, a bushing 53 is provided between the sliding sleeve 50 and the vent nozzle 20. The bushing 53 is fixed on the through hole 51 of the sliding sleeve 50. The bushing 53 is slidably sleeved on the vent nozzle 20.

In this embodiment, the cross-section of the other end of the vent nozzle 20 facing the outside of the housing 10 gradually decreases toward the outside of the housing 10, and the cross-section of the vent 21 is constant, that is, referring to FIG. 2, the wall at the left end of the vent nozzle 20 gradually becomes thinner towards the left. Specifically, the end of the vent nozzle 20 facing the outside of the housing 10 is a hollow cylinder. The outer diameter of the hollow cylinder gradually decreases toward the outside of the housing 10, while the inner diameter is constant. A section of the vent nozzle 20 that is gradually tapered does not contact the through hole 51. The bushing 52 is located on one side of the through hole 51 facing the inside of the housing 10. The elastic member 60 is sleeved on the vent nozzle 20 and sandwiched between the first stop block 22 and the sliding sleeve 50. When no consumable connector is installed on the vent 20, the elastic member 60 is in a free or slightly compressed state. When the elastic member 60 is in a free state, both ends of the elastic member 60 are in contact with the first stop block 22 and the sliding sleeve 50, respectively.

In this embodiment, the elastic member 60 is a spring.

The magnetic block 70 is installed on the sliding sleeve 50. Specifically, the magnetic block 70 is mounted on the sliding sleeve 50 inside the housing 10.

The second circuit board 80 is installed in the housing 10, and is connected to the first circuit board 30.

The position sensor 90 is installed on the second circuit board 80, and is connected to the second circuit board 80. The installation position of the position sensor 90 meets that: after the consumable connector is installed on the vent nozzle 20, the distance that the sliding sleeve 50 slides toward the inside of the housing 10 is just enough to make the magnetic block 70 move into the detection area of the position sensor 90. Specifically, the position sensor 90 is Hall sensor. When the magnetic block 70 moves into the detection area of the position sensor 90, the position sensor 90 outputs 1; when the magnetic block 70 is not in the detection area of the position sensor 90, the position sensor 90 outputs 0.

Both the first circuit board 30 and the second circuit board 80 are connected with the external equipment, and are configured to send the detected pressure information and the signal detected by the position sensor 90 to the external equipment, and the detection data is displayed by the external equipment.

When the consumable connector is installed on the vent nozzle 30, the consumable connector will push the sliding sleeve 50 to move toward the inside of the housing 10 and compress the elastic member 60. The magnetic block 70 moves toward the inside of the housing 10 along with the sliding sleeve 50. After the consumable connector is installed on the vent nozzle 30, the magnetic block 70 moves to the detection area of the position sensor 90. After the magnetic block 70 is sensed by the position sensor 90, the output signal changes. Therefore, it can be judged whether the consumable connector is installed in the vent nozzle 30 correctly. The pressure sensor 40 detects the pressure of the gas in the vent nozzle 30, so that the pressure of the gas in the pipeline of the consumable connector connected to the vent nozzle 30 and the equipment connected to the consumable connector can be obtained. After the consumable connector is taken out, under the elastic force of the elastic member 60, the sliding sleeve 50 is returned.

The above embodiment is a preferred embodiment of the present invention, and is not intended to limit the protection scope of the present invention.

What is claimed is:

1. A pipeline pressure monitoring device, comprising:
   a housing, one side of the housing having a mounting hole;
   a vent nozzle, the vent nozzle having a vent, the vent nozzle being installed in the housing, one end of the vent nozzle extending out of the housing via the mounting hole, a first stop block being provided on the vent nozzle;
   a first circuit board, installed in the housing;
   a pressure sensor, configured to detect pressure inside the vent nozzle, the pressure sensor being installed on the first circuit board and connected to the first circuit board, the pressure sensor being matched with another end of the vent nozzle facing an inside of the housing, the pressure sensor being installed at the another end of the vent nozzle facing the inside of the housing to block the another end;
   a sliding sleeve, installed in the mounting hole in a sliding manner, the sliding sleeve having a through hole, the sliding sleeve being sleeved on the vent nozzle via the through hole, a limit member being provided on the sliding sleeve, the limit member being located inside the housing;
   an elastic member, sleeved on the vent nozzle and sandwiched between the first stop block and the sliding sleeve;
   a magnetic block, installed on the sliding sleeve;
   a second circuit board, installed in the housing and connected to the first circuit board; and
   a position sensor, installed on the second circuit board and connected to the second circuit board, wherein the installation position of the position sensor meets that: after a consumable connector is installed on the vent nozzle, the distance that the sliding sleeve slides toward the inside of the housing is just enough to make the magnetic block move into a detection area of the position sensor.

2. The pipeline pressure monitoring device as claimed in claim 1, wherein a sealing ring is provided between the pressure sensor and the vent nozzle.

3. The pipeline pressure monitoring device as claimed in claim 1, wherein the elastic member is a spring.

4. The pipeline pressure monitoring device as claimed in claim 1, wherein a bushing is provided between the sliding sleeve and the vent nozzle, the bushing is fixed on the through hole of the sliding sleeve, and the bushing is slidably sleeved on the vent nozzle.

5. The pipeline pressure monitoring device as claimed in claim 4, wherein the cross-section of the end of the vent nozzle facing an outside of the housing gradually decreases toward the outside of the housing, the cross-section of the vent is constant, a section of the vent nozzle that is gradually tapered does not contact the through hole, and the bushing is located on one side of the through hole facing the inside of the housing.

* * * * *